United States Patent [19]
Ogata et al.

[11] Patent Number: 5,740,813
[45] Date of Patent: Apr. 21, 1998

[54] METHOD OF CALCULATING WORK BURDEN INDEX AND APPARATUS FOR CARRYING OUT THE SAME METHOD AND WORK ROUTINE PLANNING METHOD UTILIZING THE SAME INDEX

[75] Inventors: Satoshi Ogata, Nagoya; Kiyoyuki Imayoshi, Toyota; Yoshinori Eri, Nagoya; Tatsuhisa Ishii, Aichi-ken; Tetsuro Konomi; Kazunari Fukumoto, both of Toyota, all of Japan

[73] Assignee: Toyota Jidosha Kabushiki Kaisha, Aichi-ken, Japan

[21] Appl. No.: 248,489

[22] Filed: May 24, 1994

[30] Foreign Application Priority Data

May 25, 1993 [JP] Japan .................................. 5-122571
Mar. 3, 1994 [JP] Japan .................................. 6-033541

[51] Int. Cl.$^6$ .......................................................... A61B 5/04
[52] U.S. Cl. ........................... 128/733; 128/774; 482/902; 395/207
[58] Field of Search ............................... 364/401, 413.01; 128/733, 774, 782; 73/379.1; 482/4–9; 601/23; 395/207, 208, 209, 211

[56] References Cited

U.S. PATENT DOCUMENTS

| | | | |
|---|---|---|---|
| 5,018,726 | 5/1991 | Yorioka | 272/129 |
| 5,301,680 | 4/1994 | Rosenberg | 128/733 |

FOREIGN PATENT DOCUMENTS

| | | | |
|---|---|---|---|
| 0074407 | 3/1981 | European Pat. Off. | A61B 5/04 |

OTHER PUBLICATIONS

Physical Therapy, V71, N1, p. 3(13) Electromyographic and Cinematographic Analysis of Movement from a Kneeling to a Standing Position in Healthy 5– to 7–year-old children, Dolio Vonder Linden, Jan. 1991.

Sato, Katsuura, Sato, Tochihara, Yokoyama et al., Human Engineering Basic Numerical Value Formulas Manual, Gihodo Shuppan, pp. 223–224, 1992.

Kogi & Hakamada, "Slowing of Surface Electromyogram and Muscle Strength in Muscle Fatigue", Rep. Inst. Labor, 60, 1962, pp. 27–41.

*Primary Examiner*—Gail O. Hayes
*Assistant Examiner*—Junghoon Kenneth Oh
*Attorney, Agent, or Firm*—Finnegan, Henderson, Farabow, Garrett & Dunner, L.L.P.

[57] ABSTRACT

In order to obtain an index which generally shows the work burden extent of various works carried out in an automobile assembling factory or the like, for each work content, the maximum muscle contraction ratio is measured after the work has been continued for 5 seconds, the work burden index (L) is calculated from the measured ratio value, and the equivalent work burden in a standard work is calculated from the calculated work burden index (L) for 5 seconds. The work burden index (TVAL) of actual work is calculated from the equivalent work burden and the actual work time. Suitably, a work routine plan is corrected such that the obtained TVAL is normalized with an apparatus comprising means for storing the equivalent work burden for each work content, means for displaying an image of the work content, and means for inputting work content parameter and so forth while watching the displayed image.

9 Claims, 17 Drawing Sheets

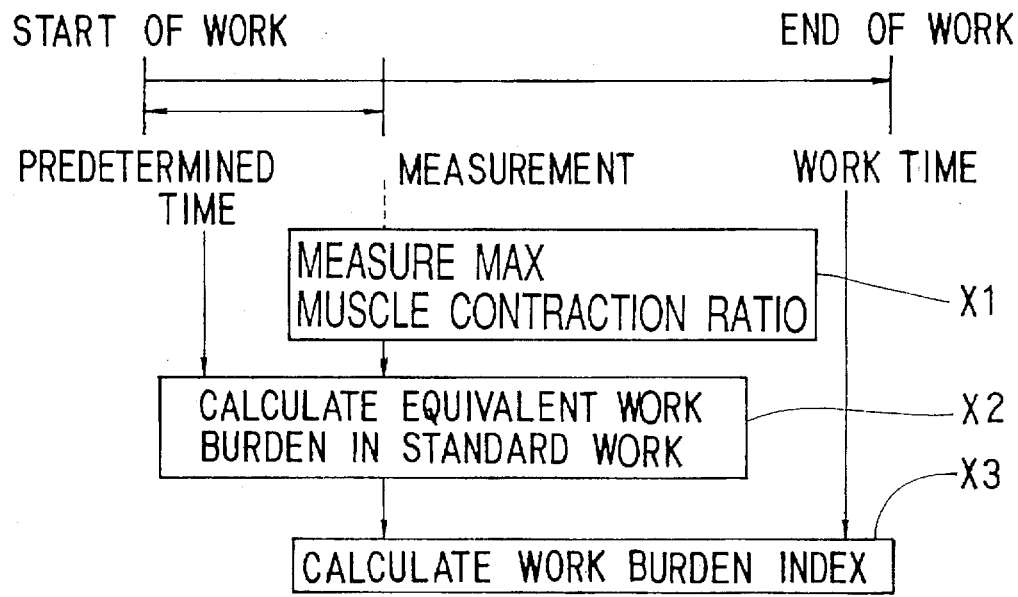
F I G. 1
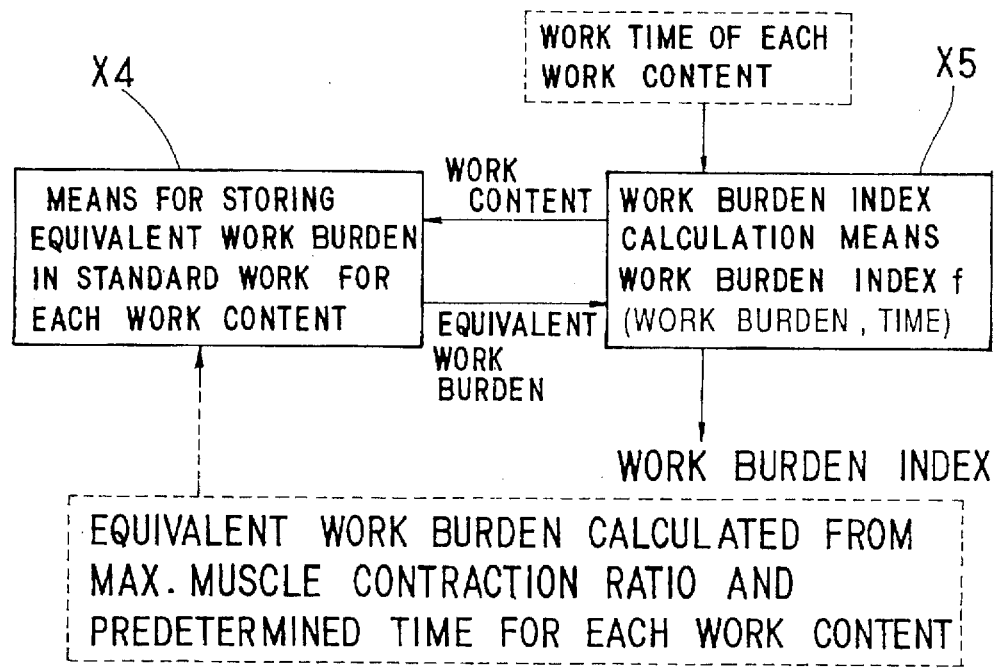
F I G. 2

FIG.7(A)

| POSITION \ DIRECTION | A FORWARD | B UPWARD | C DOWNWARD | D BACKWARD |
|---|---|---|---|---|
| 1 | ↗ | ↗ | ↗ | ↗ |
| 2 | ↗ | | ↗ | ↗ |
| 3 | ↗ | ↗ | | ↗ |

FIG.7(B)

FORWARD

| POSITION K \ LOAD WA DIRECTION OF PUSH | LEVEL 1 | LEVEL 2 | LEVEL 3 | LEVEL 4 | LEVEL 5 |
|---|---|---|---|---|---|
| 1 UPWARD | 13 | 14 | 17 | 22 | 30 |
| 2 STANDING | 11 | 12 | 14 | 16 | 18 |
| 3 STOOPING | 16 | 17 | 18 | 23 | 30 |

FIG.7(C)

FORWARD

| POSITION K \ LOAD WA DIRECTION OF PUSH | LEVEL 1 | LEVEL 2 | LEVEL 3 | LEVEL 4 | LEVEL 5 |
|---|---|---|---|---|---|
| 1 UPWARD | 31 | 32 | 35 | 39 | 45 |
| 2 STANDING | 28 | 30 | 32 | 34 | 36 |
| 3 STOOPING | 34 | 35 | 36 | 40 | 45 |

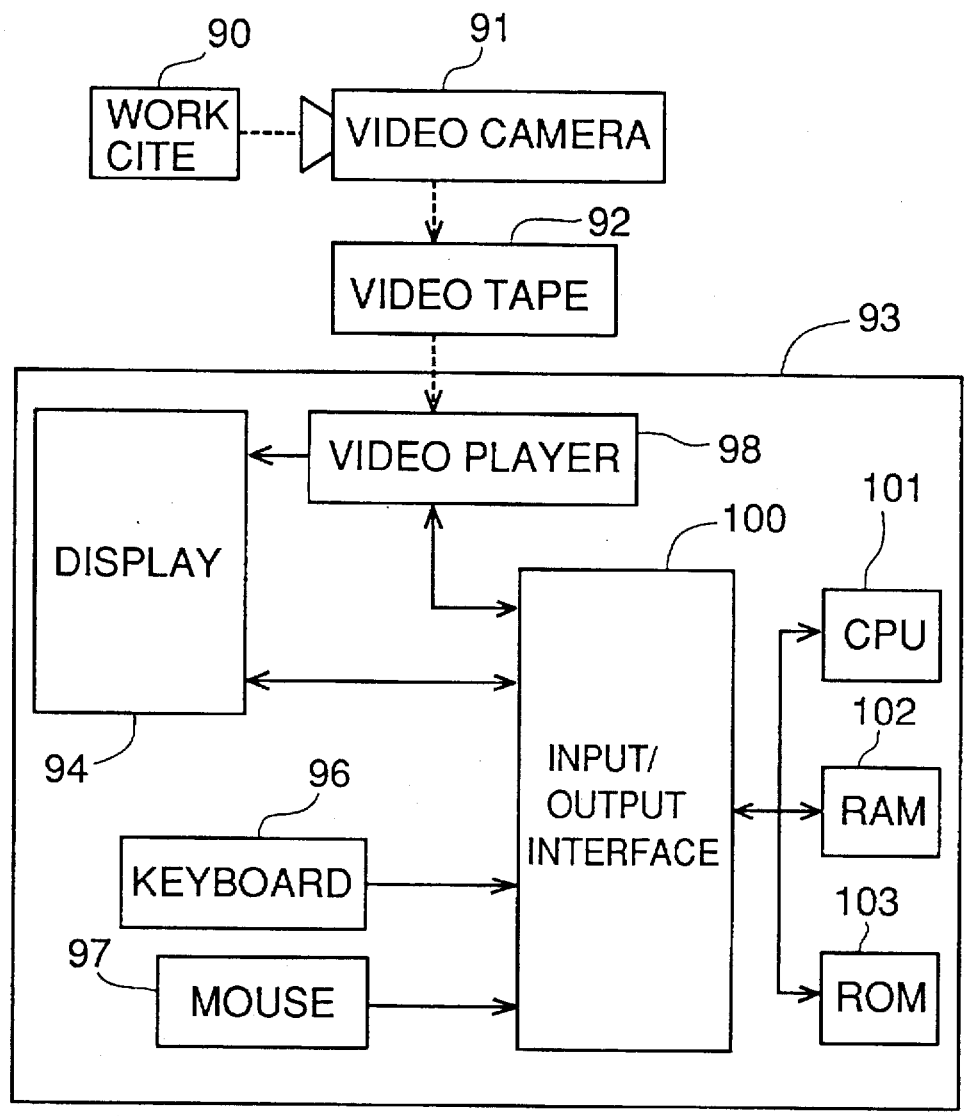
F I G . 1 2

FIG. 14

| a | b | c | d | e | f | g | h | i | j | k | l | m | n | | | o | TVAL | |
|---|---|---|---|---|---|---|---|---|---|---|---|---|---|---|---|---|---|---|
| | | | | | | | | | | | | | | | | | p | q |
| T1 | 312 | 4 | 43 | SETTING OF FR DOOR G/N | 3 | 6 | 3.2 | 5.0 | 2 | - | 0 | - | 95.9 | 104 | 106 | ○ | - | 36.8 |
| T1 | 312 | 4 | 44 | FITTING OF FR DOOR G/N | 4 | 6 | 1.5 | 2.0 | 2 | 0 | 0 | 20 | 97.9 | 105 | 112 | ○ | 18.2 | 40.0 |
| T1 | 312 | 4 | 45 | TAKING OF IMPACT | 3 | 6 | 1.0 | 1.7 | 2 | - | 1.0 | - | 99.6 | 112 | 120 | | - | 42.5 |
| T1 | 312 | 4 | 46 | SETTING OF SCREW IN IMPACT | 3 | 6 | 2.1 | 3.0 | 2 | - | 1.0 | - | 102.6 | 120 | 128 | | - | 43.0 |
| T1 | 312 | 4 | 47 | SETTING OF IMPACT | 3 | 6 | 1.5 | 3.0 | 2 | - | 1.0 | - | 105.6 | 128 | 131 | ○ | - | 45.0 |
| | | | | | | | | | | | | | | 131 | 138 | | | |

| LINE | GROUP | RL | PART NAME | QUANTITY | WEIGHT | REFERENCE | MOUNTING POSITION | | | TREADLE PLATE | BOLT NUT | | | FITTING | | |
|---|---|---|---|---|---|---|---|---|---|---|---|---|---|---|---|---|
| | | | | | | | L | W | H | | NUMBER | LOAD | NUMBER | NUMBER | DIRECTION | LOAD |
| 1 | 3 | 312-01 | L | FOOD SUPPORT CLAMP | 1 | 0.4 | 1 | 200 | -200 | 550 | 0 | 0 | 0 | 0 | 0 | 0 |
| 1 | 3 | 312-02 | L | RR OUTSIDE HANDLE L | 1 | 0.5 | 2 | 250 | -800 | 600 | 0 | 2 | S9 | 0 | 0 | 0 |
| | | 171b | | 171c  171d | r | s | t | u | v | w | x | y | z | α | β | γ |
| 1 | 7 | 312-03 | R | RR OUTSIDE HANDLE R | 1 | 0.5 | 2 | 250 | 805 | 600 | 0 | 2 | S9 | 0 | 0 | 0 |
| | | .... | .... | .... | .... | .... | .... | .... | .... | .... | .... | .... | .... | .... | .... | .... |
| 1 | 3 | 312-07 | R | LAGGAGE W/S | 1 | 0 | 3 | 0 | 0 | 400 | 0 | 0 | 0 | 64 | 0.2 | 15 |

FIG. 17

METHOD OF CALCULATING WORK BURDEN INDEX AND APPARATUS FOR CARRYING OUT THE SAME METHOD AND WORK ROUTINE PLANNING METHOD UTILIZING THE SAME INDEX

BACKGROUND OF THE INVENTION

1. Field of the Invention

This invention relates to a technique of calculating an index which permits evaluation of the extent of burden that is borne by workers in works carried out in automobile assembling factories and the like. The invention also relates to a technique of evaluating burdens in irrational and illogical work sharing or work routine on the basis of calculated work burden index, thus permitting the planning of more comfortable and efficient work routines.

2. Description of the Prior Art

The extent of the work burden borne by the worker is substantially dependent on two factors, i.e., the hardness of work and the duration thereof. As a suitable index indicative of the hardness of work, maximum muscle contraction ratio is used. The maximum muscle contraction ratio is obtained by measuring slight potential generated in the muscle when the muscle shrinks, and it is the ratio of the potential during work to the potential at the time of the maximum shrinkage of the muscle. It can be measured electrically and objectively.

It is well known in the art that when the maximum muscle contraction ratio M is used to indicate the hardness of work, the extent of burden that is imposed on the worker can be well represented by the work burden index L given in the following equation (1) (Kogi & Hakamada "Slowing of Surface Electromyogram and Muscle Strength in Muscle Fatigue", Rep. Inst. Labor. 60, p-p. 27–41, 1962, Sato, Katsuura, Sato, Tochihara, Yokoyama et al "Human Engineering Basic Numerical Value Formulas Manual", p-p. 223–224, 1992, Gihodo Shuppan).

$$L = C_1 \log t + C_2 \log M - 48.06 \quad (1)$$

where L is the index which is also called the living body burden extent and well corresponds to the extent of burden felt by the worker, and t is the duration of work.

It is confirmed that C1 and C2 in equation (1) are constants, and it is also well known that C1 and C2 are $$C1 = 27.03 \text{ and } C2 = 53.78 \quad (2)$$

It is further confirmed that equations (1) and (2) hold independently of the kind of muscle, the worker's position, etc. ("Human Engineering Basic Numerical Value Formulas Manual" noted above, Endo "Evaluation of Static Muscular Fatigue", Japanese Journal of Human Engineering, Vol. 17, No. 3, p-p. 123–127, 1981). Furthermore, equations (1) and (2) hold independently of the kind of work or work content.

The work burden index is obtainable by equations (1) and (2), if the maximum muscle contraction ratio M is not changed during work. However, in long works such as automobile assembling works, the maximum muscle contraction ratio M is changed during the work. In usual works, the work burden is constant. When the work with a constant work burden is continued, the maximum muscle contraction ratio is changed with the lapse of time. Therefore, in the case of a long work with a constant work burden, it is inadequate to obtain the work burden index by using equation (1).

Meanwhile, the hardness of work can also be represented by the work burden W. It is well known that when the hardness of work is represented by the work burden W, the work burden index can be calculated from the following equation (3) (Oshima "Studies on Fatigue", p-p. 89–92, Dobun Shoin, Oshima "Labor Burden and Its Tolerances", 1953, Gakken Text).

$$L = d_1 \log t + d_2 \log W - 162.0 \quad (3)$$

where t is the duration of work, and W is the work burden. In the case of the above equation (1), the coefficients C1 and C2 are constant irrespective of the work contents. However, it is well known that in the case of equation (3) representing the hardness of work in terms of the work burden, the coefficients $d_1$ and $d_2$ are variables depending on the worker's position and the contents of work. Therefore, when it is intended to calculate the work burden index for various work contents by using equation (3), it is necessary to determine the coefficients $d_1$ and $d_2$ for each worker's position and also for each work content. To do so is actually almost impossible. This is so because it requires enormous experiments for each work content to determine the coefficients $d_1$ and $d_2$.

As is seen from the foregoing, up to date there is no practically applicable technique of calculating an index which permits accurate evaluation of the work burden extent in various works. More specifically, with equation (1), although there is no need of taking the work content differences into considerations, correct indexes can not be obtained for works subject to maximum muscle contraction ratio changes during the work time. (Actually there are many such works.) With equation (3), correct indexes are obtainable for long works as well. In this case, however, it is necessary to obtain the coefficients for each work content, which is substantially impractical under such situations that the work has versatile contents. This is so because the determination of the coefficients $d_1$ and $d_2$ requires enormous experiments for each work content.

SUMMARY OF THE INVENTION

The invention has been attained in combining the above two techniques and developing a new technique which permits accurate calculation of a work burden index indicative of the extent of burden borne by the worker in various works subject to maximum muscle contraction ratio changes during the work time.

According to the invention, there is provided a method of work burden index calculation which, as schematically shown in FIG. 1, comprises a step X1 for measuring the maximum muscle contraction ratio when a work has been continued for a predetermined time, a step X2 for calculating, from the maximum muscle contraction ratio measured in the step X1 and the predetermined time noted above, an equivalent work burden in a standard work providing the same work burden index as a work burden index when the work is continued for the predetermined time, and a step X3 for calculating, from the calculated equivalent work burden and an actual work time, the work burden index when the work is continued for the actual work time.

In equation (3) which relates the work burden index L, the work burden W and the work duration t to one another, it is sufficiently possible to calculate the coefficients $d_1$ and $d_2$ if the work content is fixed. For example, it was reported that it was found from an experiment with bicycle ergometer as shown in FIG. 3 that in the work of pedaling the bicycle ergometer $$d_{1S}=25.51 \text{ and } d_{2S}=117.6 \quad (4)$$

(Ohshima "Studies on Fatigue", p-p. 82–92, Dobun Shoin). In equation (4), S indicates the pertaining to the work of pedaling the bicycle ergometer.

The work, in which the coefficients $d_1$ and $d_2$ are known as above, may be made a standard work.

In the method according to the invention, a work has been continued for a predetermined time, and the maximum muscle contraction ratio at that time is measured in step X1. The predetermined time may be set such that for this time the maximum muscle contraction ratio is not substantially changed during the work. Thus, if the maximum muscle contraction ratio is MA when a work with a work burden WA is done, the work burden index LA when the work is continued for the predetermined time t is, from equations (2), $$LA=27.03\times\log t+53.78\times\log MA-48.06 \quad (5)$$

and, from equation (3), $$LA=d_{1A}\times\log t+d_{2A}\times\log WA-162.0 \quad (6).$$

The values of the work burden index that are obtained with equations (5) and (6) must be equal.

With the standard work, the coefficients $d_1$ and $d_2$ are known. When a work of pedaling a bicycle ergometer with a work burden Ws is made a standard work, the work burden index L is, from equations (3) and (4), $$L=25.51\times\log t+117.6\times\log Ws-162.0 \quad (7).$$

Then, it is possible to determine, from equations (5) and (7), the work burden Ws* in a standard work providing the same work burden index as the work burden index LA of a measured work. That is, Ws* can be determined from an equation $$27.03\times\log t+53.78\times\log MA-48.06=25.51\times\log t+117.6\times\log Ws^*-162.0 \quad (8)$$

By solving equation (8), we have $$Ws^*=9.311\times t^{0.0129}\times MA^{0.457} \quad (9)$$

From equation (9), Ws* can be obtained.

Ws* thus obtained means that the work burden index LA is when a work with maximum muscle contraction ratio MA continued for time t and the work burden index when a standard work with work burden Ws* is continued for time t are equal. That is, the work burden Ws* means one in a standard work providing the same work burden index as that of a work with the maximum muscle contraction ratio MA. In other words, the work burden Ws* is an equivalent work burden in a standard work which provides the same work burden index L as the work burden index for the work of the maximum muscle contraction ratio MA.

According to the invention, the equivalent work burden in the standard work is calculated in step X2 from the measured maximum muscle contraction ratio MA and predetermined time t on the basis of the above concept. If the standard work is to pedal the bicycle ergometer, the equivalent work burden is calculated by using equation (9). The standard work may be any work so long as the coefficients $d_1$ and $d_2$ are known and may not be the work of pedaling the bicycle ergometer.

When the equivalent work burden Ws* in the standard work providing the same work burden index as that of the measured work has been calculated, the index indicative of the extent of work burden when the work is continued for a certain actual work time is calculated from the coefficients $d_{1S}$ and $d_{2S}$ in the standard work, the actual work time and equation (3). If the standard work is to pedal the bicycle ergometer, the index indicative of the extent of work burden is calculated by substituting the equivalent work burden that is calculated in equation (9) into the right side of equation (8). This calculation is carried out in step X3.

Thus, by the method according to the invention, the equivalent work burden in a standard work providing the same work burden index as the work burden index calculated from the measured maximum muscle contraction ratio can be calculated for various works, and thus it is possible to calculate the index indicative of the work burden extent uniformly in terms of the work burden in a standard work.

According to the invention, there is also provided a work burden index calculation apparatus which, as schematically shown in FIG. 2, comprises storage means X4 for storing, for each work content, data of equivalent work burden in a standard work providing the same work burden index as that calculated from the maximum muscle contraction ratio when the work is continued for a predetermined time and from the predetermined time, and means X5 for inputting actual work time of each work content, retrieving the equivalent work burden for the inputted work content from the storage means X4, and calculating and outputting the work burden index of the work content by substituting the retrieved equivalent work burden and actual work time into an equation for work burden index calculation from work burden and work time.

With the work burden index calculation apparatus which is schematically shown in FIG. 2, the equivalent work burden is determined and stored for each work content, and thus by inputting work content and work time, the work burden index when the work is continued for the work time is calculated and outputted.

According to the invention, there is further provided a work burden index calculation apparatus which, as schematically shown in FIG. 9, comprises storage means X6 for storing, for each work content, data of equivalent work burden in a standard work providing the same work burden index, display means X7 for displaying images showing work status, input means X8 for inputting work content parameter and work time concerning the work displayed on the display means X7, calculation means X9 for calculating the work burden index of the work content from the work time inputted and the equivalent work burden corresponding to the inputted work content parameter, and display means X10 for displaying the calculated work burden index.

With the work burden index calculation apparatus which is schematically shown in FIG. 9, it is possible to input work content parameter and work time in a state with video image of the actual work status displayed on the display means X7, that is, while visually confirming the work content status with the parameter and other data to be inputted therefore. The apparatus thus can be handled extremely conveniently.

According to the invention, there is further provided a work burden index calculation apparatus which, as schematically shown in FIG. 10, comprises storage means X12 for storing, for each work content, data of equivalent work burden in a standard work providing the same work burden index, video display means X13 for video display of the work status and capable of tentatively stopping the display, input means X14 for inputting work content parameter and work time of the work displayed on the video display means X13, calculation means X15 for calculating the work burden index of the work content from the work time inputted and the equivalent work burden corresponding to the inputted work content parameter, and storage means X16 for storing the inputted work content parameter, the work time, the calculated work burden index and still image information indicative of the work status corresponding to the inputted work content such that these items are related to one another.

With the work burden index calculation apparatus, which is schematically shown in FIG. 10, in addition to obtaining improved operation control character of the data input operation as described in connection to FIG. 9, "still image information", "work content parameter and work time" and "work burden index" are stored in the storage means X16 such that they are related to one another. It is thus possible to very readily carry out the work burden extent analysis operation. For example, when a work with a high work burden index is found, the work with high work burden extent can be visually recognized by retrieving for the pertinent still image information. Or it is possible to readily know the pertinent work content parameter and work time.

According to another aspect of the invention, there is provided a method of planning a work routine or work sharing by using the work burden index that is calculated in the above way. The method, as schematically shown in FIG. 11, comprises a step X17 for calculating, for each work content, the equivalent work burden in a standard work providing the same work burden index, a step X18 for inputting, for each work unit, work content parameter and work time, a calculation step X19 for calculating, for each work unit, the work burden index thereof from the inputted work content parameter and work time, and a correction step (i.e., a loop of step X20, X21 and X19) for correcting the work unit until the calculated work burden index is normalized.

The method which is schematically shown in FIG. 11, permits re-evaluation of the work routine or work sharing by using the work burden index that is calculated in the above way. For example, with a work unit with a work burden index above a permissible value, it is possible to make the index to be below the permissible value by dividing the work unit. Conversely, with two or more works units with small work burden indexes, these works units may be combined into a single work unit, so that it is possible to improve the operation control character. In this way, the method permits planning a satisfactory work routine while accommodating the extent of work burden borne by the worker in an adequate range.

The present invention will be more fully understood from the following detailed description and appended claims when taken with the accompanying drawings.

BRIEF DESCRIPTION OF THE DRAWINGS

FIG. 1 is a schematic view illustrating a method of work burden index calculation;

FIG. 2 is a schematic view showing an apparatus of work burden index calculation;

FIGS. 7(A) to 7(C) are views showing an example of work contents, pertinent mean maximum muscle contraction ratio and equivalent work burden;

FIG. 12 is a block diagram showing the construction of an embodiment of the apparatus;

FIG. 14 is a view showing input data and so forth;

FIG. 17 is a data list for TVAL calculation;

DETAILED DESCRIPTION OF THE PREFERRED EMBODIMENTS

Figure 3:
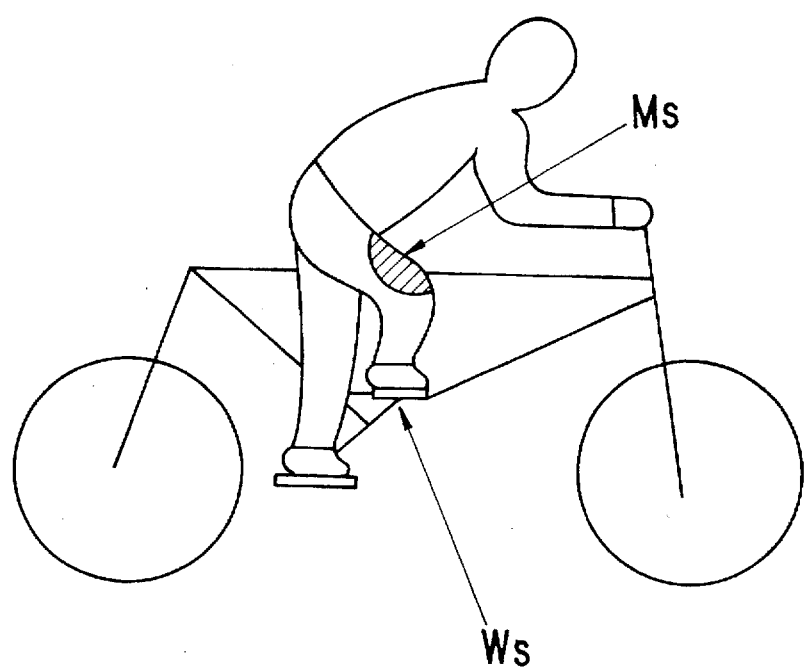
FIG. 3 is a view showing an example of standard work.
Figure 4:
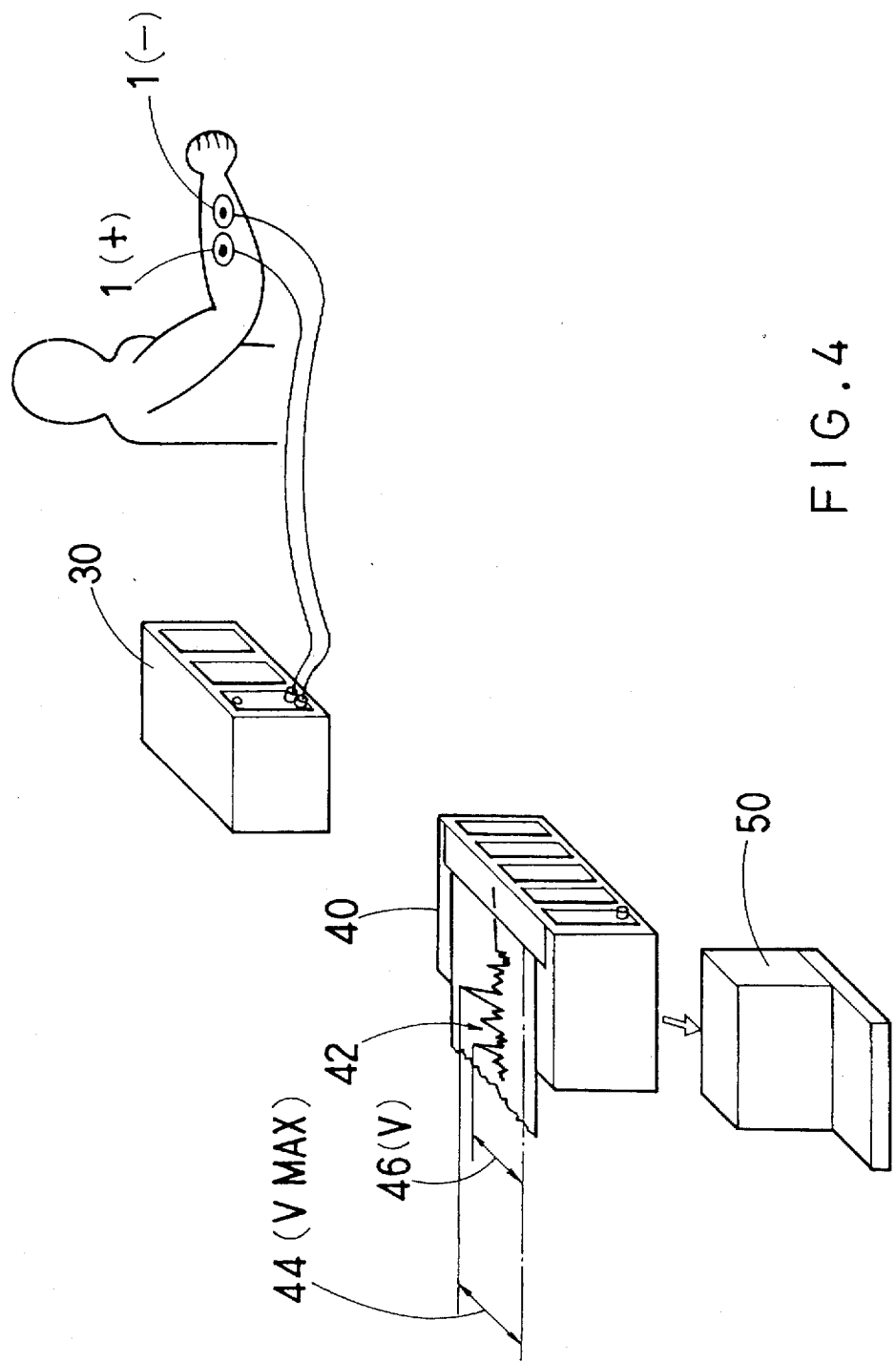
FIG. 4 is a view showing the construction of an embodiment of the apparatus.
Figure 5:
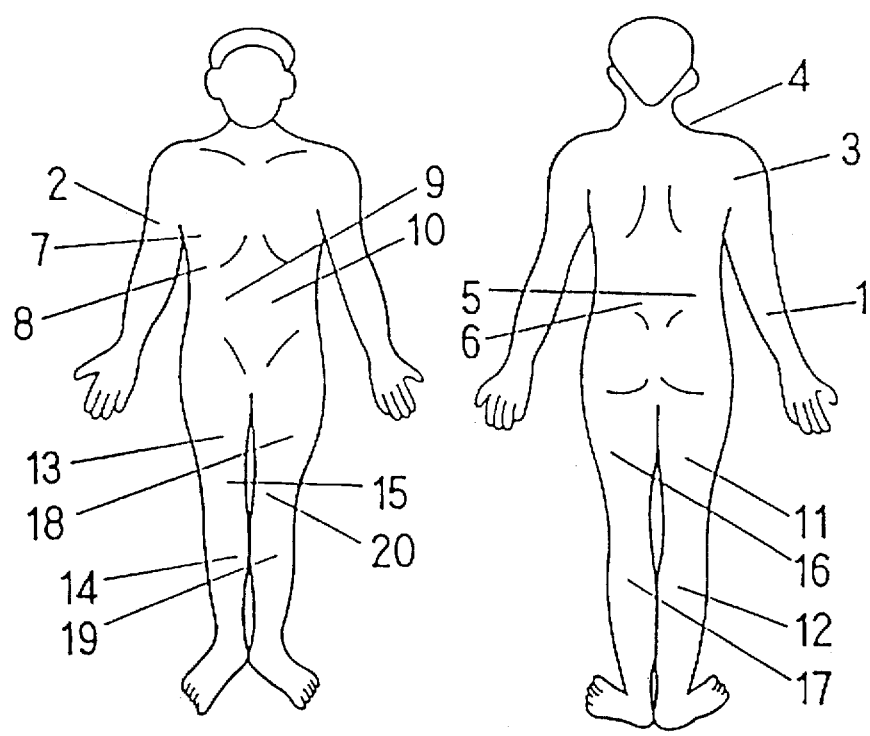
FIG. 5 is a view showing muscle potential measurement positions and muscles under measurement.

FIG. 4 schematically shows the construction of an apparatus embodying the invention. Referring to FIG. 4, shown at 1(+) and 1(−) are paired electrodes for measuring the muscle potential. Twenty pairs of such electrodes are used for the measurement of the maximum muscle contraction ratio. The 20 pairs of electrodes are attached to the worker under test at respective 20 positions as shown in FIG. 5(A). These electrode pairs attached to positions 1 to 20 detect the muscle potentials across muscles as listed in the table of FIG. 5(B).

Although only a single pair of electrodes is shown for the simplicity of illustration, actually, signals representing muscle potentials as detected by the 20 electrode pairs are inputted to and amplified by an amplifier 30 and fed to a printer 40. The printer 40 outputs the measured muscle potential change matter as graph 42. Although only a single graph is shown in FIG. 4, actually 20 such graphs are outputted.

After setting the 20 electrode pairs on the worker under test, the measurement is started. First, the muscle potentials VMAX(1) to VMAX(20) at the time of the maximum shrinkage of the muscle are measured for the 20 different muscles (step S2 in FIG. 6). Then, the maximum muscle contraction ratios M(1) to M(20) are measured. The measurement is done after the worker has worked continuously for 5 seconds for each work content. The work contents are defined as combinations of worker's positions 1 to 3 in FIG. 7(A), directions A to D in which the worker applies force in each of the positions noted above, levels 1 to 5 of the applied force, etc. FIG. 7(A) shows only a part of work contents, and there are many work contents not shown in FIG. 7(A).

For instance, denoting the work which is carried out with an upward position shown in row 1 in FIG. 7(A) and by applying forward force of level 1 shown in FIG. 7(B), by work content A, muscle potentials VA(1) to VA(20) that are detected when the work content A has been continued for 5 seconds are measured. The maximum muscle contraction ratios are determined by using equations $$MA(1) = VA(1)/VMAX(1) \times 100,$$
$$\vdots$$
$$MA(20) = VA(20)/VMAX(20) \times 100$$

Figure 6:
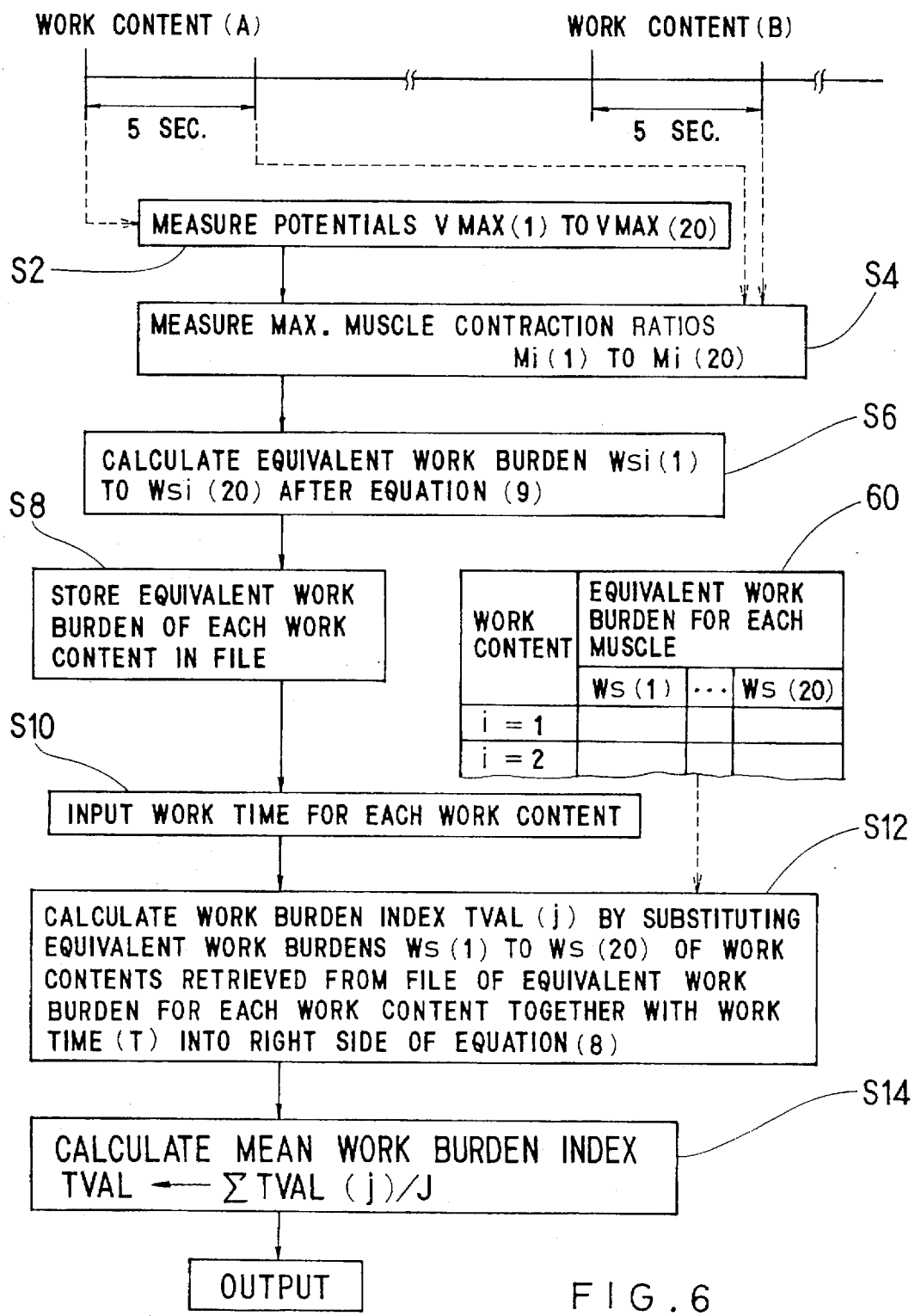
FIG. 6 is a view showing processing contents.

(step S4 in FIG. 6). MA(1), ...., MA(20) represent the muscle potentials (i.e., 20 muscle potentials corresponding to the 20 different muscles) after 5 seconds.

When the measurement concerning one work content is completed, the work content is then changed, and then the muscle potentials are measured again after 5 seconds, and the maximum muscle contraction ratios are determined (step S4 in FIG. 6).

In this way, the maximum muscle contraction ratio MA(1) to MA(20) is determined for work content A, the maximum muscle contraction ratio MB(1) to MB(20), for work content B, and the maximum muscle contraction ration MC(1) to MC(20), for work content C (step S4 in FIG. 6). In step S4, the subscript i indicates the work content, and the subscripts 1 to 20 indicates muscle kind measured.

The work time is set to 5 seconds, because during the work as long as about 5 seconds, the maximum muscle contraction ratio is not substantially changed. Thus, in this case, the work burden index Li,j is determined from equations (1) and (2) to be $$Li,j = 27.03 \times \log 5 + 53.78 \times Mi,j - 48.06$$

where i indicates the work content, and j (1 to 20) indicates the muscle kind.

When the work burden index Li,j for each muscle is determined for each work content, the equivalent work burden Ws*i,j in a standard work content providing the same work burden index Li,j for each muscle is calculated using equation (7). It is also possible to calculate the equivalent work burden Ws*i,j directly from equation (9) as shown in step S6 in FIG. 6. Here, s indicates the standard work, i the actual work content, and j the muscle kind. When the equivalent work burden Ws*i,j is obtained in this way, it is stored in file in step S8.

In the file, as shown at 60 in FIG. 6, the equivalent work burden in a standard work is stored in correspondence to each actual work content and each muscle kind. The process after step S6 in FIG. 6 is executed in the computer 50 shown in FIG. 4. The file 60, in which the equivalent work burden is stored for each work content and each muscle kind, is formed in a memory of the computer 50.

For the evaluation of the overall work burden extent of work, the analysis for each muscle is not essential. It is possible to take the average of the values obtained for the 20 different muscle kinds for each work content. FIG. 7(B) shows part of data of the average value of the maximum muscle contraction ratios for the individual muscle kinds for each work content that is determined by the position, load level and direction of push. FIG. 7(C) shows part of the average value of the calculated equivalent work burdens. In this case, the equivalent work burden is calculated for level zero work as well. i.e., the work in which the worker maintains the position thereof.

Up to the above step, the calculation of the equivalent work burden in a standard work for each work content is completed. The equivalent work burden in the standard work as calculated for each work content in the above way, is stored in the storage means (i.e., file) 60. As noted above, either value for each muscle kind or the average value may be stored in the file 60. FIG. 6 shows an example in which values are stored for the individual muscle kinds.

Then, the work content and actual work time of an actual work are inputted to the computer 50 in step S10. For example, in FIG. 8, it is inputted that a work in which the worker maintains a much stoop position is started at instant T1 and ended at instant T2. Also, it is inputted that a work in which the worker applies a force of level 5 forward in a much stoop position is started at instant T3 and ended at instant T4 (step 10 in FIG. 6). For the former work, retrieval is made for the equivalent work burden corresponding to the former work content, and the work burden index TVAL is calculated by substitution of the detected equivalent work burden into the right side of equation (8). The work burden index calculated here is not obtained directly from the maximum muscle contraction ratio or work burden, but it is obtained after conversion to the equivalent work burden in the standard work. The index obtained for the latter is made TVAL.

As is seen from the form of equation (8), the work burden index increases exponentially with the lapse of time, and a curve of graph 80 is obtained. This curve shows the manner of changes in TVAL with time for the work content of maintaining the much stoop position. In this illustrated case, the index when the work is ended has a value of 42. Meanwhile, similar process is executed for the latter work. As a result, a curve of graph 82 is obtained.

Figure 8:
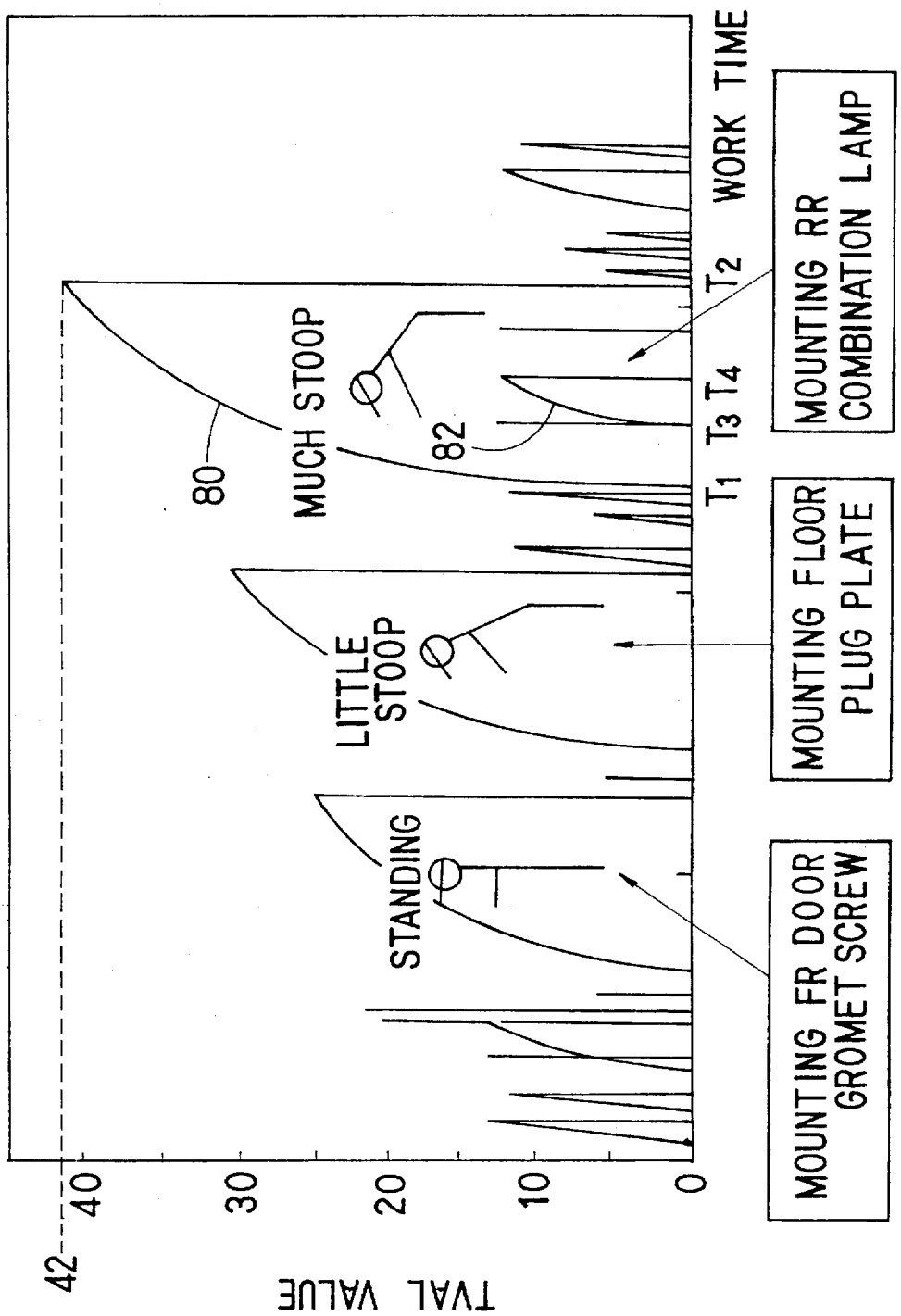
FIG. 8 is a graph showing an example of index TVAL of actual work.
Figure 9:
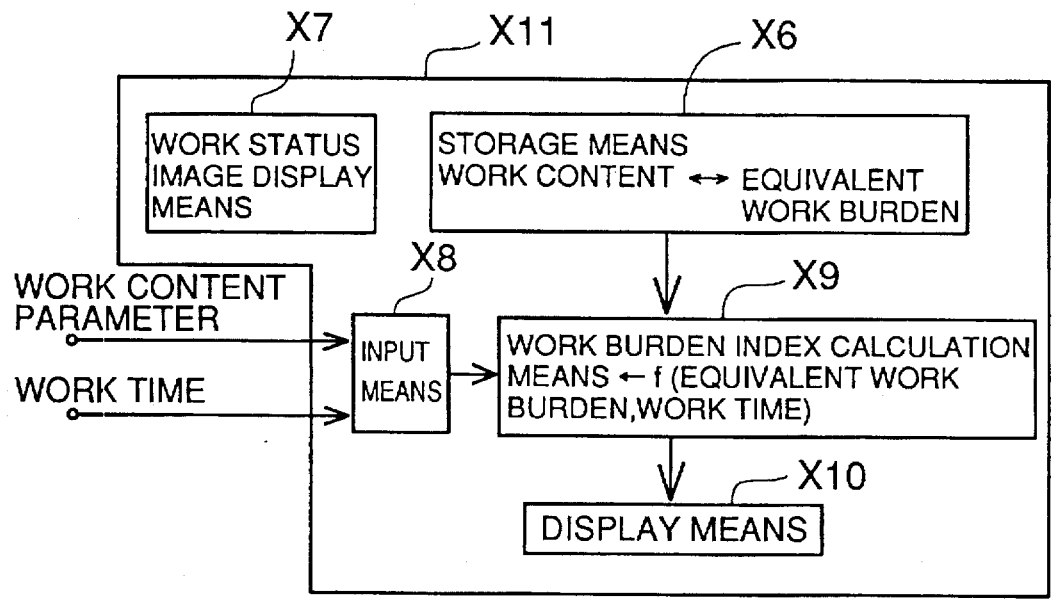
FIG. 9 is a schematic view showing a work burden index calculation apparatus.
Figure 10:
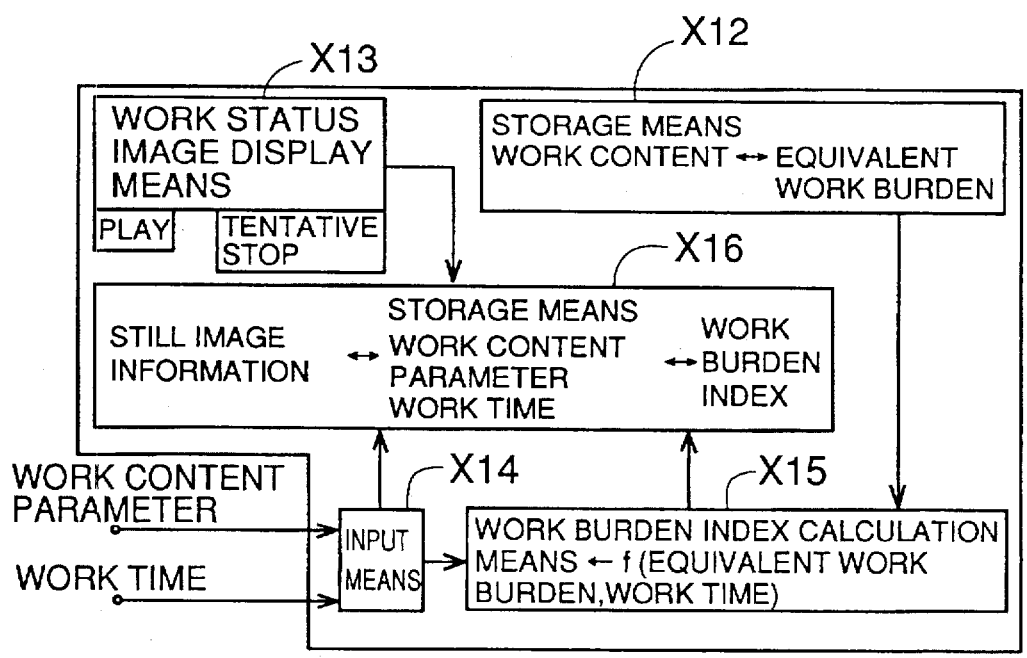
FIG. 10 is a schematic view showing a work burden index calculation apparatus.

Comparing the former and latter, in the latter, the duration is short although the equivalent work burden is high, and thus the index at the time of the end of the work is large in the former. The other curves in FIG. 8 are obtained like the curves 80 and 82.

In step S12 in FIG. 6, the work burden indexes are obtained for the individual muscle kinds and are averaged in step S14. In this way, the work burden index TVLA (i, j) is obtained for each work content and also for each muscle kind, and by averaging these values, the work burden indexes of the whole work can be obtained. Where the overall evaluation alone is needed, the index may be obtained from the averaged equivalent work burden in step S12.

The index for evaluation which is calculated at the end of the work (referred to as TVLA) well coincides with the extent of work burden felt by the worker. In the case of FIG. 8, the work burden is felt to be high in the long work started at instant T1 rather than in the short operation started at instant T3. Sometimes, the level of the graph obtained with the short work as shown at 82 may be high compared to that of the graph obtained with the long work as shown at 80. In such case, the worker feels that the work burden is higher in the hard and short work.

That is, it is recognized that the work burden index TVAL which is calculated according to the invention, well matches the worker's feeling and is a generally adequate index.

In this embodiment, a 5-second measurement is done preliminarily for each work content, and the equivalent work burden for that work content is calculated. Thus, in the actual work, a correct work burden index is obtainable for a short work lasting within 5 seconds. Further, for a composite work, for instance a work in which a work of maintaining a much stoop position is compounded with another work, it is possible to calculate the work burden index for each component work, and the burden of the actual work can be generally and analytically readily grasped.

Now, a work burden index calculation system which has been produced particularly for the invention will be described. FIG. 12 shows the system briefly. In the system, video information of a work cite 90 which is picked up by a video camera 91 on a video tape 92, can be used. The system 93 is a combination of a video system and a computer system, and it comprises a video player 98 and a display 94. The video player 98 is connected via an input/output interface 100 to the computer system including a CPU 101. To the computer system, the display 94 is connected along with a keyboard 96 and a mouse 97 via the input/output interface 100. In the computer system, a RAM 102 and a ROM 103 are connected to the CPU 101 via a bus.

Figure 13:
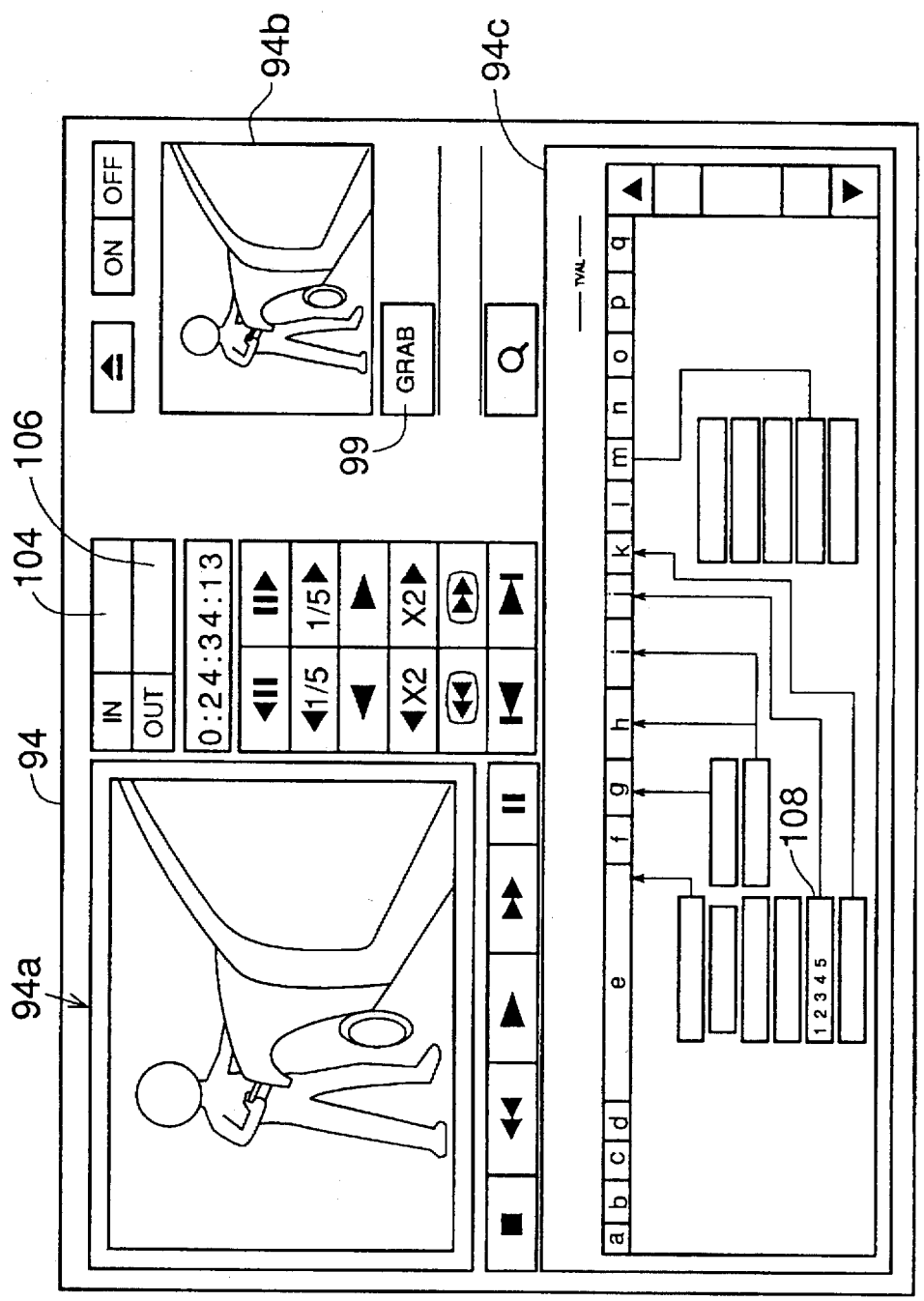
FIG. 13 is an example of display on a display screen.

FIG. 13 shows an example of display screen of the display 94 in the system 93. On a left upper area 94a of the display screen, video information from the video player 98 is displayed. Near the area 94a are provided grabs for the video player 98, i.e., a play grab, a temporary stop grab, a fast feed grab, etc., which are to be clicked with a mouse 97.

An area 94b is used for mostly displaying still images on it. An area 94c is used for mostly displaying and inputting work content parameter, work time, etc. FIG. 13 shows a display state when the operator inputs the work content parameter, work time, etc. while video information of the work status from the video player 98 is displayed the area 94a. The data input operation will now be described.

The operator first specifies with the keyboard 96 the line (a), the group (b) and the routine (c) to which data to be inputted belongs. The illustrated example deals with a work which belongs to line A3 (a), group No. 413 (b) and routine No. 6 (c). When the input operation is ended, the operator starts play-back with the video system. The video player 98 is operated by clicking the grabs displayed on the screen 94 with the mouse 97.

The operator specifies the instant of start of a work element with the mouse 97 while watching the video display on the area 94a. The video frame No. at this time is displayed on an IN column 104. The example of FIG. 13 shows the manner of data input of work while a work element of setting a head lamp (e) is executed as work element No. 14 (d).

The operator, while watching the video display of the work element of setting the head lamp, judges the section of the work (i.e., whether the work is to set, set by nipping, couple, fit, etc.) and inputs data (f) using the mouse 97. In the illustrated example, it is shown that a work of tightening (section No. 3) is being executed. Likewise, the operator judges and inputs the section (g) to which the part used in the work belongs. In the illustrated example of FIG. 13, it is shown that a part in section No. 6 is being used (g). When a work element, for instance the work element of setting the head lamp, is ended, the operator tentatively stops the display. Then, the operator determines the title of the work (e) and inputs the determined title using the keyboard 96 and mouse 97. The illustrated example shows that the work is given a title (e) of setting head lamp. While the work is actually done, a general work title such as "set" or "tighten" is displayed as grab display on the screen. Data "head lamp" is inputted using the keyboard 96, and data "set" is inputted using the mouse 97. When a general work title is inputted, the column of the work section (e) is set automatically.

When the display 94a is tentatively stopped after the end of one work element, the operator counts the number of operations (i) of the work element. In the case of a work of stretching and contracting the hands, for instance, the number of operations is the sum of the number of operations of stretching the hands and the number of operations of contracting the hands. As the number of operations, an is operation executed in 0.6 second by the average worker is given a number of 1; for instance, the operation of stretching the hands is given a number of 1.3 (0.78 sec.). When inputting the operation number data, an operation number table for each operation is displayed on the display 94, and the operator can count the number of operations with reference to this table. In the illustrated case, the work element (e) of setting a head lamp is executed with an operation number of 3.4 (i). There are works with unknown operation numbers. In such cases, the actual work time (h) is calculated to replace the operation number (i). When the operator tentatively stops the display after the end of the work element, the prevailing video frame No. is displayed on an OUT column 106. In the illustrated case, it is shown that the worker on video worked substantially at an average speed and that the actual work has been ended in a period of time (2.8 seconds, (h)) substantially corresponding to the operation number (which is 3.4, (i)).

The operation number or the actual work time is used for the calculation of the work burden index TVAL. If all the workers work at the same speed, it is possible to calculate the accurate TVAL from the actual work time (h). Actually, however, the work is done at quick and slow paces, and the work speed that is displayed in video may not be a standard one. Meanwhile, the operation number (i) is counted based on the standard work speed. Thus, a work of which the operation number is determined, is dealt with such that the work time determined from the operation number represents the actual work time. This work time is used to calculate TVAL.

As noted above, to calculate TVAL, the work content is necessary in addition to the work time. Now, the manner of data input to this end will be described. First, the operator judges the worker's position by watching the video display of the work status on the area 94a and inputs the position (j) by using the mouse 97. There is a display "1, 2, . . . " in a row 108. The operator inputs the number corresponding to the position by clicking it with the mouse 97. In the illustrated example, it is shown that the work is done in the upright position (of position No. 2, (j)). Then, the direction of force (k) applied by the worker inputted in a similar way. In the illustrated example, it is shown that the worker applies force forward (i.e., in direction No. 0, (k)) in the work of setting the head lamp. Then, the weight (mounting wright) of part (l) and coupling load (m) (i.e., load necessary for coupling) are inputted. The data inputted in this instance corresponds to the input of the level of force required for the worker.

The direction of the load is not inputted depending on the work content. For example, the extent of work burden in a work of tightening is independent of the force direction, and hence the direction of the load has no influence on the TVAL calculation. The coupling load may be inputted indirectly by specifying the kind of tool. For example, in the case of a work using a torque wrench, once the tool is determined, the coupling load is substantially determined.

With the input of data for each work element in the above data input process, the work time (which is the operation number (i) or actual work time (h) in this case) and the work content parameter (which is the position (j), the load direction (k), the mounting weight (l) and the coupling weight (m)) are inputted and stored in the RAM 102. During the data input operation, the operator can operate a still image take-in grab 99 in the presence of a display of a work status which seems to be necessary when making analysis in the future. With the click of the grab 99, the prevailing video information is stored in the RAM 102. At this time, still image information is stored in the RAM 102 such that it is related to a corresponding work element, and when the work element is specified, the still image can be read out from the RAM 102.

FIG. 14 shows an example of data inputted as a result of the above data input operation. Circle marks in a still image data column indicate that the pertinent still image information is stored in the RAM 102. Editing functions are provided for correcting, deleting, adding, etc. of data.

When the work content is specified by the position (j), direction of force (k) and magnitude thereof (l, m), retrieval is made for the equivalent work burden in a standard work as described before in connection with FIGS. 6 and 7. A one-to-one correspondence table of the work content and the corresponding equivalent work burden is stored in the ROM 103. The work burden index TVAL of the pertinent work element is calculated from the retrieved equivalent work burden and the standard work time calculated from the operation number (or the actual work time). TVAL is not calculated for a column in which it is clear that TVAL is small due to low force level.

As noted above, among the works are those which are done by maintaining the position. Accordingly, in the TVAL calculation process, the work time is divided with reference to position data into each period during which the same position is maintained. Then, TVAL of the work done by maintaining the position is calculated for each division period. The division period is shown on the rightmost column in FIG. 14. It will be seen that TVAL is increased gradually owing to the keeping of the position (of No. 2). The calculated value of TVAL is stored for each work element in the RAM 102.

Figure 15:
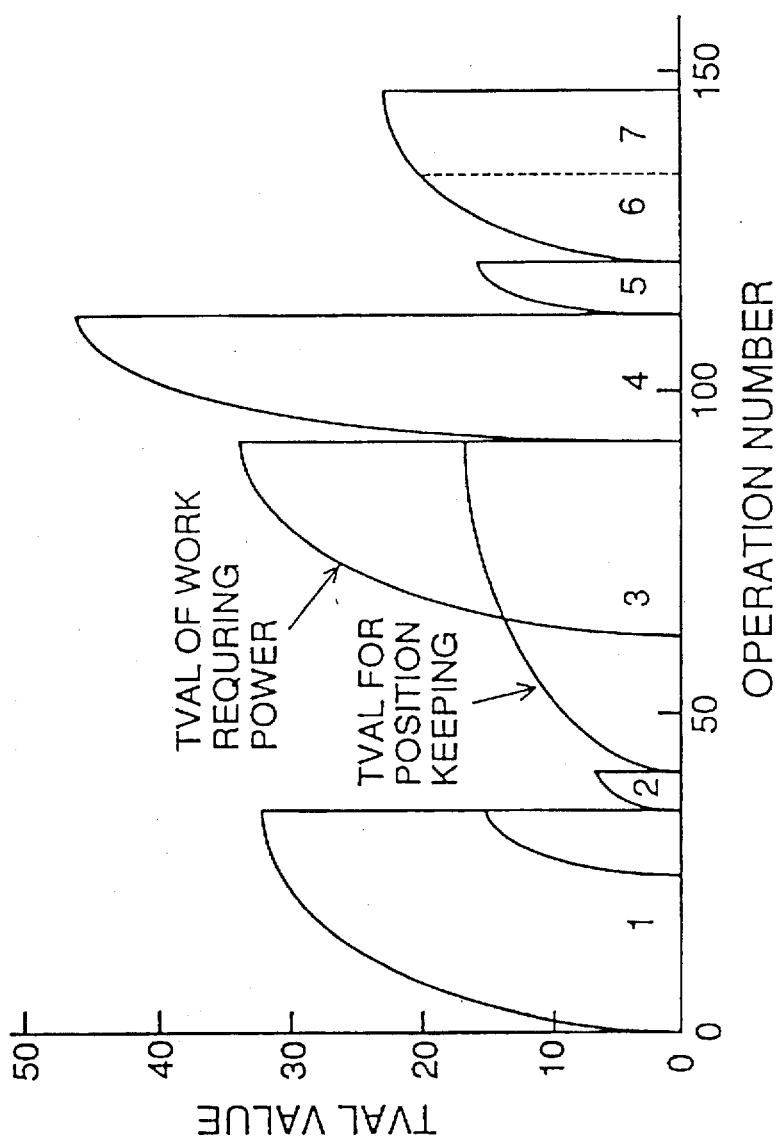
FIG. 15 is a graph showing an example of graphical display of calculated TVAL.

FIG. 15 is a graph with the ordinate taken for the calculated value of TVAL and the ordinate for the accumulated operation number. This graph is displayed on the display 94. The graph shows both TVAL of work of maintaining the position and that of work of applying force.

When the graph is displayed, the operator can grasp the extent and trend of the work burden borne by the worker in relation to the accumulated operation number.

Further, once the graph is displayed, the operator can designate a particular point on the graph with the mouse 97. When this is done, the work element which is providing the designated TVAL is specified, and the parameter, etc. of that work element are displayed on the display 94 (see FIG. 14). When the operator designates still image display, the still image of the work element is displayed on the display 94. The operator thus can visually have accurate knowledge of the extent of the work burden and the work content.

Figure 16:
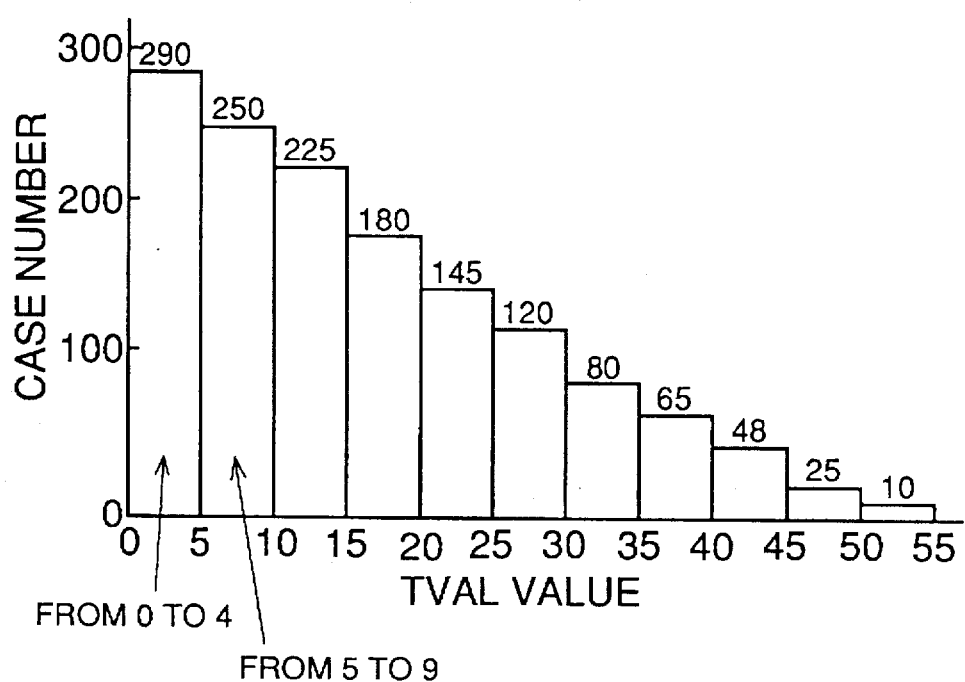
FIG. 16 is a graph showing another example of graphical display of calculated TVAL.

As an analysis tool, the operator can display the graph in FIG. 16 on the display 94. The graph is a histogram of TVAL, and from this histogram, it is possible to readily have knowledge of the frequency of appearance of hard works and extents of work burdens.

Now, a technique of planning a work routine by utilizing the work burden index TVAL calculated in the above way will be described. This embodiment deals with a case of planning in advance a work routine for assembling an automobile to be produced. A case is taken in which the video tape described before in connection with the previous embodiment is absent.

Figure 19:
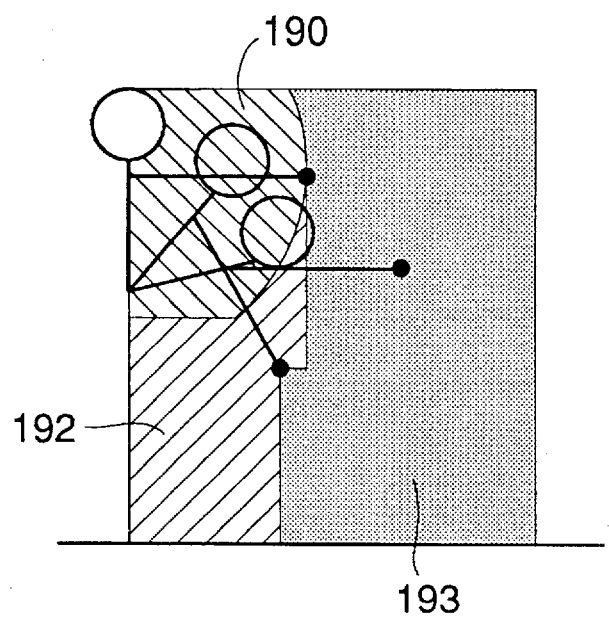
FIG. 19 is a view showing a position scale.
Figure 20:
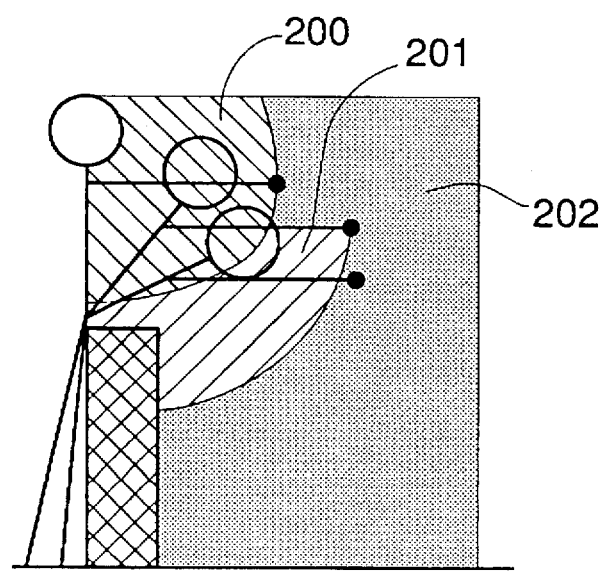
FIG. 20 is a view showing another position scale.

FIG. 17 is an example of plan of tentative work routine. For example, the second row 171 in FIG. 17 shows that a work of mounting a Rr outside handle L is planned on the left side of a vehicle (171c) in line No. 13 (171a), group No. 312-02 (171b). In this planned work, the worker, using a part with a weight of 0.5 g (s), tightens two nuts (y) at a position side-wise of the vehicle (t, standard position No. 2) with a 6S torque wrench (z). It is also shown that the mounting position is at 250 mm (u) in the longitudinal direction of the vehicle, at 800 mm (v) in the width direction and at 600 mm (w) in the height direction. When these data are provided, the worker's position is determined by position scales as shown in FIGS. 19 and 20. The scale shown in FIG. 19 is in the case of absence of any obstacle between the worker and the vehicle, such as when the worker works at a position side-wise of the vehicle. When the work position is in a zone 190, the worker works in the standing position. When the work position is in a zone 192, the worker works in a little stoop position. When the work position is in a zone 193, the worker works in a much stoop position. The scale shown in FIG. 20 is in the case of presence of an obstacle between the worker and the vehicle, such as when the work is done in a trunk room. In a work zone 200, the worker works at a standing position. In a work zone 201, the worker works in a little stoop position. In a work zone 202, the works in a much stoop position.

In the tightening work, the direction of force is irrelevant to TVAL. In addition, if it is known to make tightening with the 6S tool, the necessary level of force applied by the worker is also known. In the above way, the work content is judged from the table. Further, the standard work time is known from the quantity of parts and the kind of work.

Thus, TVAL can be determined from the table of FIG. 17, and it is possible to obtain a graph similar to those described earlier (see FIG. 18(A)).

Figure 11:
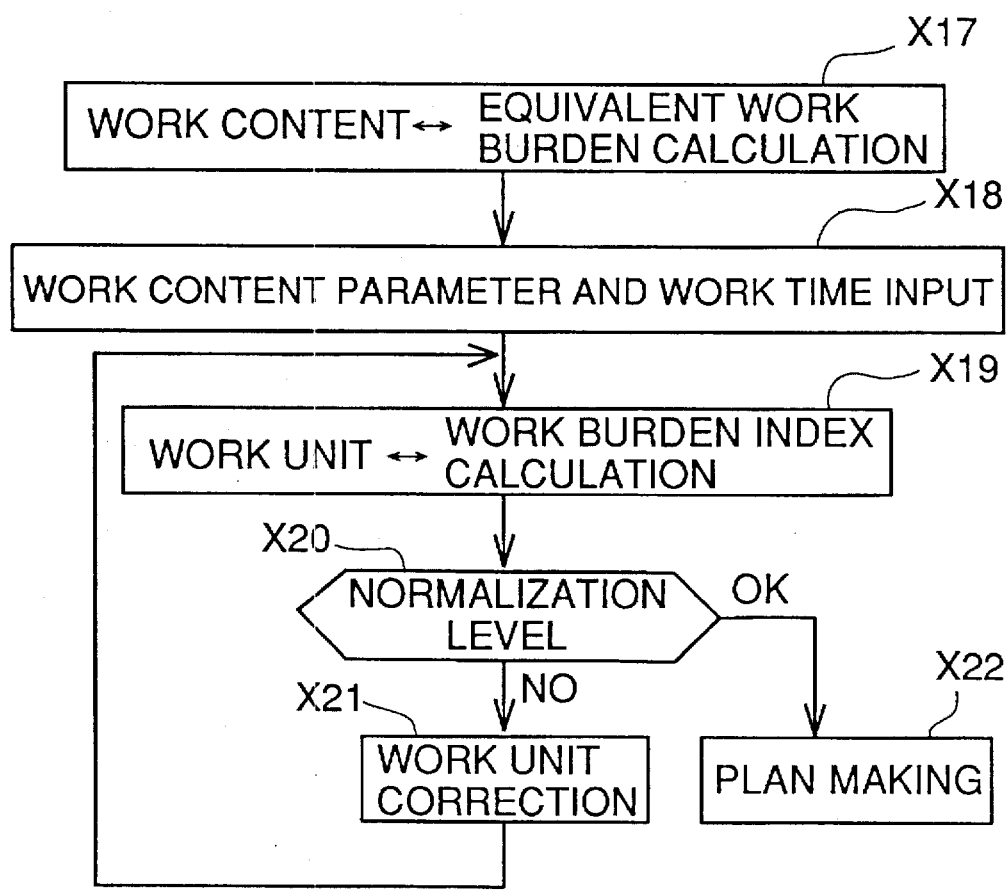
FIG. 11 is a schematic view illustrating a method of work routine planning.
Figure 18A:
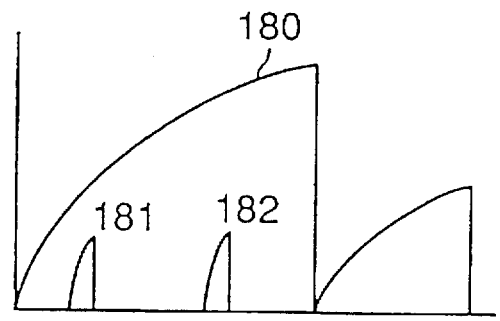
FIGS. 18(A) to 18(C) are views illustrating changes in the graphical display of calculated TVAL with routine correction.

FIG. 18(A) shows a case in which a work requiring force application is done two times while maintaining a position (the corresponding TVAL being shown at 180). In this case, TVAL concerning the position keeping is greater, and in consequence, the worker bears a great burden to maintain the position. If TVAL obtained in this way is not varied so much for each work element or work unit but is in a predetermined uniformalized range, the re-evaluation of the work routine plan is unnecessary (which corresponds to OK in step X20 in FIG. 11). However, if TVAL of the element work element or work unit is extremely great so that the uniformalization is insufficient, re-evaluation is necessary (which corresponds to NO in step X21 in FIG. 11).

Figure 18B:
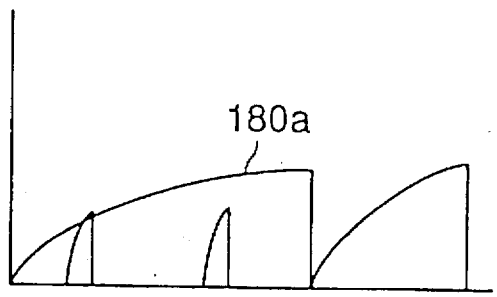
Figure 18C:
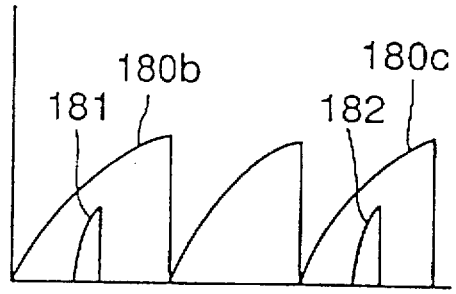

There are various processes of the TVAL uniformalizaiton. FIG. 18(B) shows a case in which the work burden can be alleviated by providing a platform at the work position and thus changing the worker's position. By utilizing the platform, the numerical figure in the column of H in FIG. 17 can be substantially changed to change the worker's position. When this is effective for the TVAL uniformalization, the work routine plan can be uniformalized. Further, it is possible to change TVAL by changing the work procedure. FIG. 18 shows a case in which the work procedure is changed by changing the position during the work. It is shown that uniformalization is obtainable by reducing the duration of a position. By correcting the work or work unit in the above way, it is possible to considerably uniformalize the work burden index for each work unit.

Where work routine correction is ineffective, the TVAL uniformalization may be realized by design change of the vehicle itself. Particularly suitably, TVAL is obtained for the work being actually done, and a work of which the obtained TVAL is particularly great, is re-evaluated when a new car model is designed. Doing so permits a rational and waste-free plan which is extremely desirable.

As has been described in the foregoing, according to the invention, it is possible to eliminate the necessity of determining, for each work content, the coefficients $d_1$ and $d_2$ holding between the work burden and the extent thereof.

the measurement of which require enormous experiments. Besides, while the determination of the work burden extent from the maximum muscle contraction ratio makes it impossible to calculate correct index of a work subject to changes in the maximum muscle contraction ratio, it is made possible to calculate the correct index by conversion to equivalent work burden in a standard work.

Thus, according to the invention it is possible to calculate the correct work burden index of a variety of works and readily find out irradiation works or illogical work distributions. Further, it is possible to plan work routines which are comfortable to the worker. The invention thus can find various applications in the industry.

While the invention has been described with reference to a preferred embodiment thereof, it is to be understood that modifications or variations may be easily made without departing from the scope of the present invention which is defined by the appended claims.

What is claimed is:

1. A method of calculating a work burden index comprising the steps of:
   measuring the maximum muscle contraction ratio when a work has been continued for a predetermined time;
   calculating, from said measured maximum muscle contraction ratio and said predetermined time, an equivalent work burden in a standard work wherein a work burden index calculated from the measured maximum muscle contraction ratio and the predetermined time is equal to a work burden index calculated from the equivalent work burden in the standard work and the predetermined time, and wherein a relation between the work burden index, work time, and work burden is known in said standard work; and
   calculating, from said equivalent work burden and an actual work time, the work burden index when the work is continued for said actual work time.

2. An apparatus for calculating a work burden index comprising:
   means for measuring a maximum muscle contraction ratio when a work has been continued for a predetermined time;
   means for calculating, from said measured maximum muscle contraction ratio and said predetermined time, an equivalent work burden in a standard work wherein a work burden index calculated from the measured maximum muscle contraction ratio and the predetermined time is equal to a work burden index calculated from the equivalent work burden in the standard work and the predetermined time, and wherein a relation between the work burden index, work time, and work burden is known in said standard work;
   means for storing the calculated equivalent work burden in a standard work; and
   means for calculating, from said equivalent work burden and an actual work time, the work burden index when the work is continued for said actual work time.

3. The apparatus as defined in claim 2, further comprising:
   display means for displaying images of work status; and
   input means for inputting a work content parameter and the actual work time concerning the display of work status on said display means.

4. The apparatus as defined in claim 2, further comprising:
   video display means for video display of work status and capable of tentatively stopping the display; and
   input means for inputting work content parameter and the actual work time of the work that is displayed on said video display means.

5. A method of planning a work routine comprising the steps of:
   measuring a maximum muscle contraction ratio when a work content has been continued for a predetermined time;
   calculating, from said measured maximum muscle contraction ratio and said predetermined time, an equivalent work burden in a standard work, wherein a work burden index calculated from the measured maximum muscle contraction ratio and the predetermined time is equal to a work burden index calculated from the equivalent work burden in the standard work and the predetermined time, and wherein a relation between the work burden index, work time, and work burden is known in said standard work;
   inputting, for each work unit, a work content parameter and an actual work time;
   calculating, from said equivalent work burden, the actual work time, and the inputted work content parameter, the work burden index when the work unit is continued for said actual work time; and
   correcting the work unit until the calculated work burden index is normalized.

6. An apparatus for calculating a work burden index comprising:
   means for storing, for each work content, data of an equivalent work burden in a standard work,
   wherein the equivalent work burden stored in said means for storing is determined by the steps of:
      measuring a maximum muscle contraction ratio when a work has been continued for a predetermined time; and
      calculating, from said measured maximum muscle contraction ratio and said predetermined time, the equivalent work burden in the standard work,
      wherein a work burden index calculated from the measured maximum muscle contraction ratio and the predetermined time is equal to a work burden index calculated from the equivalent work burden in the standard work and the predetermined time, and wherein a relation between the work burden index, work time and work burden is known in said standard work;
   means for inputting an actual work time of each work content;
   means for retrieving the equivalent work burden for the inputted work content from said means for storing; and
   means for calculating the work burden index of said work content by substituting said retrieved equivalent work burden and said actual work time into the relation for calculating said work burden index from work burden and work time.

7. The apparatus as defined in claim 6, further comprising:
   display means for displaying images of work status; and
   input means for inputting a work content parameter and the actual work time concerning the display of work status on said display means.

8. The apparatus as defined in claim 6, further comprising:
   video display means for video display of work status and capable of tentatively stopping the display; and
   input means for inputting a work content parameter and the actual work time of the work that is displayed on said video display means.

9. A method of calculating work burden index, comprising the steps of:

measuring the maximum muscle contraction ratio (MA) when a work has been continued for a predetermined time (T);

calculating an equivalent work burden (WS) in a standard work from an equation of $C1 \times \log T + C2 \times \log MA - C_3 = d_1 \times \log 7 + d_2 \times \log W_1 S - d_3$: wherein C1, C2, C3, d1, d2 and d3 are known constants and wherein an equation of $L = d1 \times \log T + d2 \times \log Ws - d3$ is established in said standard work where L indicates work burden index, and calculating a work burden index when the work is continued for actual work time (TA) from an equation of $L = d1 \times \log TA + d2 \times \log Ws - d3$.

* * * * *